United States Patent [19]

Belly et al.

[11] Patent Number: 4,912,035

[45] Date of Patent: Mar. 27, 1990

[54] METHOD FOR MINIMIZING INTERFERENCE BY REDUCTANTS WHEN DETECTING CELLS IN BIOLOGICAL FLUIDS

[75] Inventors: Robert T. Belly, Ithaca; Sheryl S. Sullivan, Hilton; Eric R. Schmittou, Rochester, all of N.Y.

[73] Assignee: Eastman Kodak Company, Rochester, N.Y.

[21] Appl. No.: 60,559

[22] Filed: Jun. 11, 1987

[51] Int. Cl.$^4$ .................. C12Q 1/02; C12Q 1/26; C12Q 1/04; C12N 1/02

[52] U.S. Cl. ..................................... 435/29; 435/25; 435/34; 435/36; 435/38; 435/261

[58] Field of Search ................. 435/25, 29, 34, 36, 435/38, 261

[56] References Cited

U.S. PATENT DOCUMENTS

| | | | |
|---|---|---|---|
| 3,411,887 | 11/1968 | US | 435/8 |
| 3,928,139 | 12/1975 | Dorn | 435/36 X |
| 4,045,221 | 8/1987 | Dominh | 430/203 |
| 4,525,453 | 6/1985 | Guardino et al. | 435/34 |
| 4,610,961 | 9/1986 | Guardino et al. | 435/34 |
| 4,673,637 | 6/1987 | Hyman | 435/29 |
| 4,701,420 | 10/1987 | Thundberg et al. | 435/26 |
| 4,746,607 | 5/1988 | Mura et al. | 435/25 |

FOREIGN PATENT DOCUMENTS 55-55757 4/1983 Japan .

*Primary Examiner*—David M. Naff
*Attorney, Agent, or Firm*—Doreen M. Wells

[57] ABSTRACT

A method for the determination of cells in a sample is disclosed. The sample is typically urine and the method is useful in removing interfering reductants from the sample. The method comprises the steps of:

(1) separating the cells from the sample,
(2) washing the separated cells with:
  (a) an iron(III) chelate solution and
  (b) a non-ionic surfactant solution and
(3) contacting the washed cells with a redox reagent so as to produce a detectable change due to the presence of the cells.

8 Claims, No Drawings

METHOD FOR MINIMIZING INTERFERENCE BY REDUCTANTS WHEN DETECTING CELLS IN BIOLOGICAL FLUIDS

CROSS REFERENCE TO RELATED APPLICATIONS

The present application is related to commonly assigned U.S. Ser. No. 890.051 filed July 28, 1986 by E. R. Schmittou entitled COBALT CONTAINING REAGENTS AND METHODS FOR THE DETERMINATION OF ANALYTES IN AQUEOUS FLUIDS.

BACKGROUND OF THE INVENTION

For the rapid and effective diagnosis and treatment of infectious diseases, it is desirable to be able to detect the micororganism causing the disease as rapidly as possible. Infections of the urinary tract are among the most common bacterial diseases, second in frequency only to infections of the respiratory tract. Such urinary tract infections (UTI) are usually associated with bacterial counts of 100,000 or more organisms per mL of urine, a condition referred to as significant bacteriuria.

Current laboratory methods for the detection of significatn bacteriuria are based on culturing the sample suspected of containing the microorganism. However, these methods are time consuming and require considerable clinical training and facilities.

My co-workers at the laboratories of the assignee of the present invention found that the cells indicating significant bacteriuria could be separated from the urine sample and detected using sensitive redox reagents. It was found, however, that even after sterile urine had been filtered and washed with buffer, the redox reagents were sensitive enough to detect the small amount of residual reductant that was left behind from the urine. thus, even when urine samples that contained no infection were tested, significant background densities were obtained due to extraneous reductants present. In addition, background densities varied from patient to patient.

Urine samples contain a wide variety of potentially interfering reducing agents such as glutatione, cysteine, uric acid and ascorbic acid to mention but a few.

In the determination of substances other than cells in urine, it is common to add materials to the sample before testing in order to reduce the interference caused by reducing agents. In U.S. Pat. No. 3,411,877 issued Nov. 19, 1968, there is disclosed a treatment which comprises adding to the sample an ionizable heavy metal compound. The analyte (e.g. glucose) is then determined using an oxidase enzyme (e.g. glucose oxidase). In Japanese Kokai 58-55757 published Apr. 2, 1983, there is disclosed a urine treatment which comprises adding to the sample a metal chelating compound (e.g. iron(III)ethylenediaminetetraacetic acid [iron-(III)EDTA]). Neither of these references is concerned with the problem of determining the presence of cells such as in the determination of significant bacteriuria. In both cases, the treating substance is present at the time the subsequent quantitating reaction takes place.

In the determination of cells, we have found that the treatment using iron(III)EDTA alone is not sufficient to remove all of the background due to reducing substances. For example, when sterile urine samples were washed with solutions containing only iron(III)EDTA, background was reduced somewhat but higher background densities than desired were obtained.

SUMMARY OF THE INVENTION

In accordance with the present invention there is provided a method for the determination of cells in a sample, said method comprising the steps of:
(1) separating the cells from the sample,
(2) washing the separated cells with:
   (a) an iron(III) chelate solution and
   (b) a non-ionic surfactant solution and
(3) contacting the washed cells with a redox reagent so as to produce a detectable change due to the presence of the cells.

In preferred embodiments of the invention, a wash step with buffer is included after and/or before the wash step 2).

DETAILED DESCRIPTION OF THE INVENTION

The present invention relates to the detection of cells, particularly significant bacteriuria in aqueous liquids. Although any specimen sample suspected of having bacteria therein (e.g. food, tissue, ground water, cooling water, pharmaceutical products, sewage, etc.) can be tested, the invention is particularly useful for cell detection in human and animal biological fluids (e.g. urine, spinal fluid, blood and the like as well as stool suspensions) and suspensions of human or animal tissue. The preferred biological fluid used in practicing the present invention is human urine.

By "cells" we mean to include not only microorganisms (e.g. bacteria, yeast and fungi but also other cells which might be detected by redox reagents.

The cells are first separated from the biological sample. Any method can be used such as filtration, centrifugation or precipitation. Filtration is the most convenient and is therefore preferred. In the case of urine, filtration of the urine through a filter having a pore size generally less than 0.2 micrometers is sufficient to remove the cells from the sample.

The separated cells are then washed with a solution which contains an iron(III) chelate and a solution containing a surfactant.

A wide variety of iron(III) chelates are useful. The chelate can be made by simply mixing an iron salt with a suitable ligand, many of which are known. Useful iron chelates include iron(III) chelates of the following ligands:
(a) Ethylenedinitrilotetraacetic acid (EDTA),
(b) Nitrilotriacetic acid
(c) Diethylenetriaminepentaacetic acid
(d) 1,3-Diamino-2-hydroxypropane-N,N,N',N'-tetraacetic acid
(e) 1,2-Diaminopropane-N,N,N',N'-tetraacetic acid
(f) Ethylenediamine-N,N'-diacetic acid
(g) Iminodiacetic acid
(h) N-Methyliminodiacetic acid
(i) trans-1,2-Diaminocyclohexane-N,N,N',N'-tetraacetic acid
(j) 1,3-Diaminopropane-N,N,N',N'-tetraacetic acid and salts, e.g. Na or K.

The currently preferred ligands are a, b, g and h.

In addition to the iron(III) chelate solution, the cells are also washed with a solution of non-ionic surfactant. The iron(III) chelate and the surfactant can be in the same solution or in separate solutions. Where the cells are separated from the sample by filtration, the iron(III)

chelate and the surfactant can be in the filter material in which case the wash solution is made in situ.

Useful non-ionic surfactants include octylphenoxypolyethoxy ethanols commercially available from Rohm and Haas Company under the Triton trade name (e.g. x-100, 102, 165 and 305); p-nonylphenoxypolyethoxy ethanols commercially available from Olin Mathieson Co.; polyethylene glycol ethers of alcohols available from Union Carbide Co. under the trade name Tergitol (e.g. 15-S-7 and 15-S-9); polyoxyethylene compounds, commercially available from ICI Americas, under the trade name Tween (e.g. 20, 80); and natural non-ionic surfactants. Currently preferred nonionic surfactants are Triton X-100, Triton X-405, Tween 20 and Tween 80.

The concentration of the components in the wash solutions is not critical. Typically the concentration of the iron chelate in the solution is at least about 0.001 and preferably between about 0.005 and 0.01 molar. The concentration of the surfactant is at least about 0.05% and preferably betwen 0.1 and 2%.

A wide variety of redox reagents can be used. Particularly preferred redox reagents are the cobalt(III) containing reagents described in copending commonly assigned U.S. patent application Ser. No. 890.051 filed July 28, 1986 and entitled COBALT CONTAINING REAGENTS AND METHOS FOR THE DETERMINATION OF ANALYTES IN AQUEOUS FLUIDS (previously mentioned). In this patent there is disclosed a reagent composition for the determination of cells which comprises a water soluble cobalt(III) complex, a water soluble metallizable dye and preferably an electron transfer agent and a carbon source.

Another preferred redox reagent is described in copending and commonly assigned U.S. patent application Ser. No. 824,766, filed Jan. 31, 1986, now U.S. Pat. No. 4,857,271, and entitled REDUCIBLE COMPOUNDS AND ANALYTICAL COMPOSITIONS, ELEMENTS AND MITHODS UTILIZING SAME. In this application there is disclosed benzoquinone and naphthoquinone compounds which, on reduction, release detectable species.

Another redox reagent is described in copending commonly assigned U.S. patent application Ser. No. 718,301 filed 1 Apr. 1985, now U.S. Pat. No. 4,701,420, and entitled ANALYTICAL COMPOSITIONS, ELEMENTS AND METHODS UTILIZING REDUCTION OF FERRIC ION CHELATES TO FORM DETECTABLE DYES. In this patent there is disclosed a composition which comprises a chelate of iron-(III) ions and a iron(III) coordinating ligand which produces iron(II) ions when reduced and a second iron-(II) ion coordinating ligand which preferantially coordinates iron(II) ions to form a colored complex.

Many other redox reagents are known such as the compositions containing NAD, an electron carrier and a tetrazolium salt described in U.S. Pat. No. 4,351,899; the compositions containing a polyvalent metal ion chelate, and indicator capable of reacting with the metal ion and a buffering agent described in U.S. Pat. No. 4,303,409; and compositions containing a variety of reducible compounds such as described in U.S. Pat. Nos.: 3,331,752; 3,711,252; 4,101,381; 4,116,774; 4,224,034; and 3,954,412.

As noted the presently preferred redox reagents are cobalt(III) complex containing reagents. Cobalt(III) is a trivalent metal that typically has a coordination number of six. An extremely wide variety of ligands are known to coordinate to cobalt(III). If the ligands are selected so that they contain a negative charge, a valence can be satisfied by the ligand. Conversely, if the ligand is electrically neutral, the valence must be satisfied by a non-coordinated counter-ion and a salt is formed. For use in the present invention, water soluble complexes are required. The cobalt(III) complex salts, being more water soluble, are preferred.

Useful netural ligands for forming Co(III) complexes include: ammonia; aliphatic amines, such as ethylenediamine, propylenediamine, diethylenetriamine; substituted or unsubstituted aromatic amines, such as aniline, 2-aminoethylaniline, 2,2'-bisaniline; substituted or unsubstituted heterocyclic amines, such as pyridine, 2,2'-bipyridine, 2-(aminomethyl)pyridine, 4,4'-dimethyl-2,2'-bipyridine, 2,2',2"-terpyridine, morpholine, pyrimidine, pyridazine, 2,2'-bipyrazine, quinoline, isoquinoline, acridine, thiazole, imidazole, triazine, 1,10-phenanthroline, 5-nitrophenanthroline, 2,2'-bipyrimidine, 2,2'-diimidazole; and oxygen donor ligands, e.g. amides such as N,N-dimethylformamide and water. Any anion can be used as the counter ion. For convenience, halide ions are preferred such as chloride, bromide and iodide. Other useful counter anions include, for example, azide, thiocyanate, tetrafluoroborate, nitrate, perchlorate, hexafluorophosphate, sulfate, carbonate, sulfonate and carboxylate ions.

Anionic ligands may also coorindate with cobalt(III) provided the charge on cobalt(III) is not completely neutralized by the ligands, so that the complex is a salt and therefore water soluble. Useful anionic ligands include halide, i.e., chloride, bromide, iodide or fluoride, azide, thiocyanate, nitrite, carbonate, carboxylate, sulfonate, oxalate and 2,4-pentanedionate ions.

The other component that is useful in the redox reagent useful in the present invention is a water soluble metallizable dye. A very wide variety of dyes that are capable of coordinating with a cobalt(II) and cobalt(III) ion are useful. The dyes must be water soluble. Many of the specific dyes listed in the references below are not water soluble but can be easily made so by the incorporation of a suitable solubilizing group in the dye molecule by conventional methods. Conventional solubilizing groups such as carboxylic acid, sulfonic acid and sulfate groups are useful.

Preferred dyes are also tridentate ligands for cobalt. Tridentate ligands form more stable complexes and therefore can more easily displace ligands from the cobalt(II) complex.

With these criteria in mind, useful dyes and dye classes are disclosed in U.S Pat. Nos. 4,396,546; 4,273,708; 4,272,434; 4,024,993; 4,147,544 and 4,419,435.

In the detection of cells in urine samples, it is preferred that the redox reagent also contain a carbon source for the suspected microorganism. A convenient carbon source for all of the cells which might be suspected is glucose. As with the other components, the carbon source can be included in the filter material that is used to filter the urine or in the element which carries the cobalt(III) redox reagents.

The preferred dyes are:

2-[(3-methyl-2-pyridyl)azo]-1-naphthol-4-sulfonic acid, monoammonium salt;

2-[(5-carboxy-2-pyridyl)azo]-1-naphthol-4-sulfonic acid, diammonium salt; and

2-[(3-methyl-5-sulfo-2-pyridyl)azo]-1-naphthol-4-sulfonic acid, diammonium salt.

The composition useful herein optionally, but preferably, includes an electron transfer agent (identified herein as ETA) which can transfer electrons from the cells to the cobalt(III) complex. In general, it is desirable that the ETA has a potential which is more positive than that of the reductant and less positive than that of the cobalt(III) complex.

ETA compounds useful in the practice of this invention include phenazine methosulfate, phenazine ethosulfate, and similar compounds, and substituted benzoquinones and naphthoquinones such as those described in copending and commonly assigned U.S. Ser. No. 699,374, filed Feb. 7, 1985, now U.S. Pat. No. 4,746,607, by A. J. Mura et al and entitled USE OF SUBSTITUTED QUINONE ELECTRON TRANSFER AGENTS IN ANALYTICAL DETERMINATIONS. combinations of different ETA compounds can be used if desired. The preferred ETAs are trimethyl-1,4-benzoquinone, 4,5-dimethoxy-1,2-benzoquinone and 2,3-dimethoxy-5-methyl-1,4-benzoquinone.

In a preferred mode of practicing the present invention, the urine sampe to be tested is filtered in an apparatus similar to the one disclosed in Hinckley U.S. Ser. No. 019,810 filed Feb. 27, 1987, now U.S. Pat. No. 4,833,087, entitled DISPOSABLE CONTAINER CONFIGURED TO PRODUCE UNIFORM SIGNAL. The filtered cells are washed according to the present invention and the redox reagent is then added and the presence of a color change is determined. Where it is desired to determine the type of infection that might be present, two urine samples can be tested. One untreated sample is tested to determine the presence or absence of cells of any type. A second sample is first treated with an anionic surfactant as is described in commonly assigned U.S. Pat. No. 4,5225,453 issued June 25, 1985.

Test strips are often used as a convenient way to carry measured amounts of reagent to the test solution. The test strip is placed into a solution that might already contain the cells to be determined. The reagents dissolve from the test strip into the solution so as to form the reaction solution. In preferred embodiments of the test strips of the present invention, the reagents are carried in a water soluble binder. When the test strip is immersed into the solution, the binder dissolves releasing the reagents. For reasons not understood, this mode of delivery provides improved sensitivity in comparison to the use of freshly made solutions of the reagents. Useful water soluble polymers include N-vinylpyrrolidone polymers such as poly(N-vinyl-2-pyrrolidone) homopolymer as well as copolymers, e.g. copolymers with acrylamide such as poly(acrylamide-co-N-vinyl-2-pyrrolidone) 90:10 by weight.

When employed in dry analytical elements, the composition components can be incorporated into the absorbent carrier material by imbibition, impregnation, coating or another suitable technique. Useful absorbent carrier materials are insoluble and maintain their structural integrity when exposed to water or physiological fluids such as urine or serum. Useful absorbent carrier materials can be prepared from paper, porous particulate structures, porous polymers, cellulose, wood, glass fiber, woven and nonwoven fabrics (synthetic and nonsynthetic) and the like. A useful dry analytical element is made by imbibing a solution of the composition into the material and drying. Details for making such elements are well known in the art, as exemplified in U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

MATERIALS

In the examples below, the following materials were used. The cobalt(III) complex was (2,2'-bipyridine)-bis(1,2-diaminoethane)cobalt(III) chloride. The dye used was 2-[(5-carboxy-2-pyridyl)azo]-1-naphthol-4-sulfonic acid, diammonium salt. The surfactants were obtained from Sigma Chemical Co., St. Louis, Mo. Samples were filtered through MicroSep TM 0.5 μm cellulose acetate filters (Fisher Scientific Co., Rochester, N.Y.) in a Millipore filter apparatus (Millipore Corp., Bedford, Mass.). P300 prefilters were obtained from Nuclepore Corp., Pleasanton, Calif. Nylon microporous membranes were obtained from Pall Corp. (Glen Cove, N.Y.).

The following examples are presented for a further understanding of the invention.

EXAMPLE 1

EFFECT OF WASHES IN REDUCING INTERFERENCES IN URINES

A 1 cm$^2$ piece of cellulose acetate filter material (pore size 0.5 μm, MicroSep TM) was placed on a glass frit support); 600 microliters of urine sample was filtered through the filter at a vacuum of about 15 psi.

The filter was then washed with 500 μL of either (a) 0.05 molar potassium phosphate buffer (KPB), pH 7.8, (b) 0.01 molar Fe(III)EDTA in 0.05 molar KPB, pH 7.8, (c) 0.01 molar FE(III)EDTA, 1% Triton X-100 in 0.05 molar KPB, pH 7.8, or (d) 1% Triton X-100 in 0.05 molar KPB, pH 7.8, and then with 2 ml of 0.05 molar KPB, pH 6.8.

The filter material was removed from the frit support and placed in a 1 ml polystyrene cuvette. The cobalt cell detection reagent was prepared by adding 2.4 ml of 0.05 M KPB, pH 6.8, 0.5 ml of cobalt(III) solution (6 mM in water) to 50 μl of dye solution (7.5 mM in water) 25 μl of glucose solution (10% by weight in H$_2$O) and 25 μl of 2,3-dimethoxy-5-methyl-1,4-benzoquinone solution (0.02M in methanol). One ml of reagent was dispersed into each cuvette. The cuvettes were incubated at 37° C., and after 30 min, 200 μl of sample was removed, placed in a clear microtiter plate and read at 610 nm.

Table 1 shows the effect of a Fe(III)EDTA and a Fe(III)EDTA/Triton X-100 wash in removing interferences present in 6 urines which showed no growth on plating i.e., sterile urine. There was a clear reduction in background with the Fe(III)EDTA/TX-100 wash compared to the KPB wash control and the Fe(III)EDTA control. In additional studies, it was shown by microscopic examintion that urine 6 contained uric acid crystals which are responsible for the residual high background after treatment. The high background in urine #4 was not investigated. Since the urine was from a hospital, it is possible that this urine contained other interferents that cause the high background.

TABLE I

Effect of KPB, Fe(III)EDTA and Fe(III)EDTA/TX-100 Wash in Eliminating Interferences in Urines

| Sample | KPD Buffer (Comparative) | OD$_{610\ nm}$ KPB +FeEDTA (Comparative) | KPB +FeEDTA +TX-100 |
|---|---|---|---|
| urine #1 | 0.440 | 0.220 | 0.190 |
| urine #2 | 0.466 | 0.143 | 0.115 |
| urine #3 | 0.460 | 0.103 | 0.094 |
| urine #4 | 0.331 | 0.119 | 0.166* |
| urine #5 | 0.250 | 0.117 | 0.093 |
| urine #6 | 0.810 | 0.357 | 0.578** |
| background | 0.089 | | |

*not investigated
**contained uric acid crystals

EXAMPLE 2

EFFECT OF WASHES ON CELL RESPONSE

This example illustrates that Fe(III)EDTA and Fe(III)EDTA/TX-100 washes did not significantly affect cell responses of various organisms, except in one case: *Pseudomonas aeruginosa* which showed a decreased response with all washes.

Testing was performed as described in Example 1. Pure cultures of the organisms were added to the urine samples. Results are shown in Table II.

TABLE II

Effect of Washes on Cell Response
O.D. at 610 nm after 30 minutes

| Organism | KPB | Fe(III)EDTA | Fe(III)-EDTA/TX-100 |
|---|---|---|---|
| *Escherichia coli* | 1.056 | 0.935 | 1.017 |
| *Staphyloccus aureus* | 1.020 | 1.053 | 1.072 |
| *Streptoccus faecalis* | 1.016 | 1.036 | 1.063 |
| *Klebsiella pneumoniae* | 1.023 | 1.034 | 1.030 |
| *Pseudomones aeruginosa* | 0.745 | 0.578 | 0.524 |

EXAMPLES 3-6

COATINGS OF COBALT(III) REDOX REAGENTS

Cobalt (III) redox reagents were carried in a coating illustrated schematically as follows:

| Cobalt Chemistry Coating | g/m$^2$ |
|---|---|
| Poly(acrylamide-co-N—vinyl-2-pyrrolidone), 90:10 | 1.1 |
| Zonyl FSN | 0.22 |
| Dye 2-((5-carboxy-2-pyridyl)azo)-1-naphthol-4-sulfonic acid, diammonium salt | 1.1 |
| Poly(ethylene terephthalate) | |
| Poly(acrylamide-co-N—vinyl-2-pyrrolidone), 90:10 | 1.1 |
| Zonyl FSN | 0.22 |
| 2,3-Dimethoxy-4-methyl-1,4-benzoquinone | 0.8 |
| Glucose | 2.2 |
| Cobalt Complex (2,2'-Bipyridine)bis(1,2-diaminoethane)cobalt(III) chloride | 16.2 |

PROCEDURE

Fresh urine samples (500 μL) were vacuum filtered through MicroSep TM filters. One urine sample was washed initially with buffer alone (500 μL); others were washed initially with Fe(III)EDTA in buffer (500 μL) or Fe(III)EDTA and surfactant in buffer (500 μL). This initial wash was followed by a buffer wash (500 μL). Solution control washes contained all appropriate components except urine. Control wash procedures were buffer (500 μL), solution control wash (500 μL), and buffer (500 μL). These controls also received an additional buffer wash (500 μL).

After the samples were applied and washed, the filter membranes were transferred to 1 mL cuvettes. In a dark area, 1 cm$^2$ pieces of the cobalt chemistry coatings were placed in tubes containing 3 mL of 0.05 M KP buffer (pH 7.0) at 37° C. to dissolve the components out of the coating; 1 mL of the resulting solution was added to the above cuvettes and the absorbances were read at 610 nm at 37° C. after 30 minutes for controls and tests.

Results, shown in Table III, indicate that backgrounds were reduced by Fe(III)EDTA and surfactant washes.

TABLE III

| Example | Solution | Background Absorbance (610 nm, 30 min) |
|---|---|---|
| Control | (Urine with buffer wash) | 0.466 |
| Control | (Urine with Buffer + Fe(III)EDTA wash) | 0.101 |
| 3 | Urine with buffer, Fe(III)-EDTA, TX-100 wash | 0.065 |
| 4 | Urine with buffer, Fe(III)-EDTA, TX-405 wash | 0.084 |
| 5 | Urine with buffer, Fe(III)-EDTA, Tween 20 wash | 0.059 |
| 6 | Urine with buffer, Fe(III)-EDTA, Tween 80 wash | 0.074 |

EXAMPLE 7

COMPARISON OF HOSPITAL URINES

A comparison of hospital urines screened with the cobalt(III) redox reagent in the presence and absence of a 0.005 molar Fe(III)EDTA/Triton X-100 wash is shown in Table IV.

The following procedure was used in screening the hospital urines: a nylon microporous membrane (0.45 μm average pore size) was incorporated into a test well of a disposable test device, similar to the one described in Hinckley, referenced above. In addition a P300 prefilter was placed in the disposable to filter off larger contaminants in the urines.

(1) a solution of Fe(III)EDTA/TX-100 (0.1 mL of 0.005 molar Fe(III)EDTA containing 0.1% TX-100) was added to the test well and allowed to filter through with about 18 psi vacuum;

(2) urine (0.5 mL) was added to the well and allowed to filter through;

(3) a wash solution containing 0.5 mL of 0.005 molar Fe(III)EDTA containing 0.1% TX-100 was added was allowed to filter through;

(4) the test well was then washed with 0.5 mL and 1.0 mL of potassium phosphate buffer, pH 6.8;

(5) cobalt reagents were reconsituted from thin film elements described in Examples 3-6 by dissolving portions (1 cm$^2$) of these elements in 3 mL of 0.05 molar KP buffer, pH 7.0; 0.5 mL of the solution was added to the well (vent closed) and the disposable was incubated at 35° C. for 30 minutes;

(6) 0.2 mL of the solution on top of the filter was removed and transferred to a clear microtiter plate and the optical density at 610 nm was measured.

For control studies, 0.05 M KPB, pH 6.8 was substituted for the Fe(III)EDTA/TX-100 in steps (1) and (3).

Results of several determinations both in the presence and absence of a Fe(III)EDTA/TX-100 wash are shown in Table IV as the average of these determinations. In addition to these solution studies, the same urine samples were plated on growth plates and evaluated in a conventional manner for quantity and type of microorganism. The results from the plating are listed in Table IV.

It is clear that the Fe(III)EDTA/TX-100 wash significantly reduced background of no growth urines. This wash can therefore be used to separate the samples exhibiting microorganism growth from those that are sterile. For example, using the control wash, the growth condition in urines A and B could not be easily distinguished. (OD 0.484 vs. OD 0.458) With the wash of the invention, growth in B (OD 0.468) could be easily determined compared to no growth urine A (OD 0.172).

TABLE IV

Effect of Fe (III)EDTA/TX-100 Wash on Hospital Urines with the Cobalt(III) Redox Reagents

| Urine | Test $OD_{610\ mm}$ Fe(III)EDTA/TX-100 | Control $OD_{610\ mm}$ KPB | Plate Count org/mL |
|---|---|---|---|
| A | 0.172 | 0.484 | No growth |
| B | 0.468 | 0.458 | $10^6$ E. coli |
| C | 0.154 | 0.443 | No growth |
| D | 0.457 | 0.466 | $10^7$ Pseudomonas |
| E | 0.467 | 0.485 | $4.5 \times 10^4$ E. coli |
| F | 0.084 | 0.346 | No growth |
| G | 0.429 | 0.443 | $10^6$ E. coli |
| H | 0.443 | 0.447 | $10^6$ Bacilli |
| I | 0.431 | 0.459 | $5 \times 10^5$ Bacilli |
| J | 0.063 | 0.198 | $10^5$ Staphylococcus |

Blank at 0 min was 0.031 (average)
at 30 min was 0.041 (average)

EXAMPLES 8-17

TESTING OF ADDITONAL FE(III) CHELATES

These examples illustrate the use of additional iron(III) chelate wash solutions to reduce backgrounds. Iron(III) chelate solutions were prepared by adding solutions of 0.05 M ferric nitrate to solutions of the appropriate ligand in distilled water so that the final Fe(III) concentration was 0.005 M and the ligand concentration was 0.005 M (or 0.01 M as noted in the Table). The pH was adjusted to 6 by the addition of 0.1 M sodium bicarbonate. The solutions were allowed to set for 4 days, then sterile filtered using MicroSep ™ 0.5 μm cellulose acetate filters and a Millipore filter apparatus.

PROCEDURE

Fresh urine samples (500 μL) were vacuum filtered through 0.5 μm Microsep ™ filters, then washed with the appropriate iron(III) chelate wash solution (500 μL), then 0.05 M KPB (pH 6.8) and 1% Triton X-100 wash solution (500 μL), and lastly 500 μL of buffer wash. A urine control was washed with 500 μL of buffer, then 500 μL buffer and 1% TX-100.

The filter membranes were transferred to test tubes, and one drop of buffer (pH 7.0) was added. In a dark area, 1 cm² pieces of cobalt chemistry coatings as described for examples 3-6 were placed in tubes containing 3 mL of 0.05 M buffer (pH 7.0) at 37° C. Then 1 mL of the resulting solutions was added to the tubes containing the filter membranes; the tubes were covered and incubated at 37° C. for 30 minutes. The tubes were mixed by vortex and read at 610 nm. Results, shown in Table V, are absorbance readings after 30 minutes and indicate that other iron(III) chelates are also effective in reducing backgrounds.

TABLE V

| Example | Iron Chelate | Background Absorbance (30 minutes, 610 nm) |
|---|---|---|
| | Background control (no urine) | 0.086 |
| | Urine control (no chelate wash) | 0.270 |
| 8 | Fe(III)ethylenedinitrilotetraacetic acid; | 0.126 |
| 9 | Fe(III)nitrilotriacetic acid (0.01 M in ligand) | 0.088 |
| 10 | Fe(III)diethylenetraiminepentaacetic acid | 0.201 |
| 11 | Fe(III)-1,3-Diamino-2-hydroxy-propane-N,N,N',N'—tetraacetic acid | 0.159 |
| 12 | Fe(III)-1,2-diaminopropane-N,N,N',N'—tetraacetic acid | 0.234 |
| 13 | Fe(III)-ethylenediamine-N,N'—diacetic acid (0.01 M in ligand) | 0.205 |
| 14 | Fe(III)iminodiacetic acid (0.01 M in ligand) | 0.079 |
| 15 | Fe(III)N—methyliminodiacetic acid (0.01 M in ligand) | 0.070 |
| 16 | Fe(III)trans-1,2-diaminocyclohexane-N,N,N',N'—tetraacetic acid | 0.233 |
| 17 | Fe(III)-1,3-diaminopropane-N,N,N',N'—tetraacetic acid | 0.141 |

This invention has been described in detail with particular reference to preferred embodiments thereof, but it will be understood that variations and modifications can be effected within the spirit and scope of the invention.

What is claimed is:

1. A method for the determination of cells in a sample, said method comprising the steps of:
   (1) separating the cells from the sample,
   (2) washing the separated cells with:
      (a) an iron(III) chelate solution and
      (b) a non-ionic surfactant solution and
   (3) contacting the washed cells with a redox reagent so as to produce a detectable change due to the presence of the cells wherein said redox reagent comprises a cobalt(III) complex and a water soluble metalizable dye.

2. A method according to claim 1 further comprising a buffer wash after and/or before step 2).

3. A method according to claim 1 wherein said cells are separated from said sample by filtration.

4. A method according to claim 1 wherein said sample is urine.

5. A method according to claim 1 wherein said iron complex is Fe(III)ethylenedinitrilotetraacetic acid.

6. A method according to claim 1 wherein said surfactant is a octylphenoxypolyethoxy ethanol.

7. A method according to claim 1 wherein said redox reagent further comprises an electron transfer agent and a carbon source.

8. A method according to claim 1 wherein said cobalt(III) complex is cobalt (2,2'-bipyridine)bis(1,2-diaminoethane)cobalt(III) chloride and the water soluble metallizable dye is 2-[(5-carboxy-2-pyridyl)azo]-1-naphthol-4-sulfonic acid, diammonium salt.

* * * * *